(12) United States Patent
Sehler et al.

(10) Patent No.: US 7,030,980 B1
(45) Date of Patent: Apr. 18, 2006

(54) DIODE PUMPED INTRACAVITY LASER PARTICLE COUNTER WITH IMPROVED RELIABILITY AND REDUCED NOISE

(75) Inventors: Dwight A. Sehler, Longmont, CO (US); Todd A. Cerni, Mead, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

(21) Appl. No.: 11/025,759

(22) Filed: Dec. 29, 2004

(51) Int. Cl.
*G01N 21/00* (2006.01)

(52) U.S. Cl. .................................... 356/337
(58) Field of Classification Search ............... None
See application file for complete search history.

(56) References Cited

U.S. PATENT DOCUMENTS

| | | | |
|---|---|---|---|
| 4,728,190 A | 3/1988 | Knollenberg | |
| 4,798,465 A | 1/1989 | Knollenberg | |
| 4,893,928 A | 1/1990 | Knollenberg | |
| 5,726,753 A | 3/1998 | Sandberg | |
| 5,751,422 A | 5/1998 | Mitchell | |
| 5,889,589 A * | 3/1999 | Sandberg | 356/338 |
| 5,920,388 A * | 7/1999 | Sandberg et al. | 356/315 |
| 6,181,419 B1 * | 1/2001 | Snelling et al. | 356/335 |
| 6,768,545 B1 * | 7/2004 | Matsuda et al. | 356/338 |
| 2004/0042008 A1 | 3/2004 | Wagner et al. | |
| 2004/0080747 A1 | 4/2004 | Cerni et al. | |

* cited by examiner

*Primary Examiner*—Tu T. Nguyen
(74) *Attorney, Agent, or Firm*—Patton Boggs LLP

(57) ABSTRACT

A fluid particle counter comprising an intracavity diode pumped solid state laser having a solid state lasing material having a non-reflective coating and a concave mirror having a reflective coating, with the coatings isolated from the sample flow by Brewster windows. The laser beam is apertured by an aperture assembly including an inner aperture closest to the inlet nozzle assembly and an outer aperture farther from the inlet nozzle assembly, with the outer aperture significantly farther from the inner aperture than the inner aperture is from the inlet nozzle assembly.

18 Claims, 2 Drawing Sheets

DIODE PUMPED INTRACAVITY LASER PARTICLE COUNTER WITH IMPROVED RELIABILITY AND REDUCED NOISE

BACKGROUND OF THE INVENTION

1. Field of the Invention

The invention in general relates to light scattering particle counters, and more particular to an intracavity particle counter that utilizes a diode pumped solid state laser.

2. Statement of the Problem

The present invention relates to the science of utilizing the principles of light scattering to detect and measure the size of individual particles suspended in a fluid. In this art, each particle that is detected is counted, and an indication of the number of particle counts within a channel is provided, with each channel corresponding to a particular size range. Thus, these instruments are referred to in the art as particle counters. The relevant general background of the science of particle counters is discussed in United States Patent Publication No. 20040042008 published Mar. 4, 2004 describing an invention of Gregg A. Wagner and Thomas Bates, which published application is hereby incorporated by reference as though fully disclosed herein. Additional general background relevant to the present disclosure is also described in: U.S. Pat. No. 4,728,190 issued Mar. 1, 1988, U.S. Pat. No. 4,798,465 issued Jan. 17, 1989, and U.S. Pat. No. 4,893,928 issued Jan. 16, 1990, all to Robert G. Knollenberg; U.S. Pat. No. 5,751,422 issued May 12, 1998 in the name of John R. Mitchell; and Smith, W. J., Modern Optical Engineering, The Design Of Optical Systems, $2^{nd}$ Edition, McGraw-Hill, 1990.

The present disclosure relates to intracavity laser particle counters, so named because the fluid sample volume passes through the laser cavity. Such particle counters permit higher illumination power levels than particle counters in which the fluid sample volume is outside the laser cavity because in intracavity particle counters only a limited amount of optical energy is allowed to pass out of the cavity. In particular, this disclosure relates to intracavity particle counters utilizing a diode pumped solid state laser (DPSSL). Intracavity particle counters utilizing a DPSSL are disclosed in U.S. Pat. No. 5,889,589, issued Mar. 30, 1999 and U.S. Pat. No. 5,726,753, Mar. 10, 1998, both to Jon C. Sandberg, and both of which are incorporated by reference to the same extent as though fully disclosed herein. The foregoing two Sandberg patents describe general qualities of the DPSSL intracavity instrument, such as cavity power density.

An improved DPSSL intracavity particle counter is described in U.S. Patent Application Publication No. 20040080747, published Aug. 29, 2004 on an invention of Todd A. Cerni, Dwight A. Sehler, and Mark A. Lilly, which patent application is hereby incorporated by reference to the same extent as though fully disclosed herein. A commercial particle counter as claimed in the foregoing patent application publication has been certified by the JQA (Japan Quality Assurance Organization as achieving reliable detection of 0.065 micron standard particles (polystyrene latex spheres), at a flow rate of 1.0 CFM ($ft^3$/min), with a counting efficiency of greater than 30%. This demonstrates that this design has significantly improved sensitivity compared to the older HeNe gas laser, intracavity particle counters as described in the Sandberg references above. To achieve detection of particles less than or equal to 0.070 microns, at 1 CFM, one must achieve very high laser cavity power levels of approximately 1000 W with a 1 W pump diode. A key component which allows for such very high power levels, is the use of ultra low loss thin film optical coatings on all laser cavity components. For instance, mirror coatings typically depart from 100% reflectance by only 20–40 parts per million (ppm). The thin film coating on the pump side of the solid state laser crystal and on the concave mirror, exhibit extremely high reflectance at the solid state laser wavelength (typically 1047–1074 nm). The optical coating on the pump side of the laser crystal, also exhibits high transmission at the pump wavelength (typically 797–808 nm). Because a laser light particle passes through or reflects from each coating billions of times a second, even a very small decrease in transmission or reflectance properties by a few parts per hundred thousand, can reduce the beam power by 50% or more. Thus, the aforementioned thin film optical coatings must remain extremely clean, as any particulate or molecular deposition will significantly reduce their performance, resulting in higher cavity losses and lower cavity power. Since, particle detection occurs intracavity, the concave mirror and inner surface of the solid state laser crystal are located in the same cavity as the sample flow. This flow may contain particulate or molecular contamination.

To maintain surface cleanliness, the prior art intracavity particle counters included filtered purge air, continually blowing across the inner surface of the laser crystal and the concave mirror; the purge process removing both particulate and molecular contamination. Still, particle counters utilizing this purge-air feature have exhibited pitting caused by particles contacting the coatings, which can result in burning of small holes into the thin film optical coatings to create pitting. Such damage cannot be repaired, and the expensive solid state laser crystals must be replaced. Since this replacement cannot be done in the field, the particle counter is off-line for an extended period.

In an intracavity DPSSL, when the pump diode is turned on, the intracavity power builds up until the pump power absorbed by the solid state laser crystal equals the sum of the fractional losses, times the intracavity power. Therefore the sum of the laser cavity losses places a fundamental limit on the amount of intracavity power that can be achieved. The laser cavity losses consist of the fractional power lost at each of the optical surfaces, plus the scattering and absorption within the laser crystal. Therefore, the DPSSL laser cavity with the fewest number of components, will likely achieve the highest intracavity power. Thus, to those skilled in the art, the pitting of the optical coatings appeared to be an insurmountable problem, since additional optical components to protect the coatings leads to reduction of laser power, and the additional optical components would likely need to be themselves coated to prevent undue diminution of the laser power, leading to a further problem ad infinitum.

The 1988 and 1990 Knollenberg patents cited above teach that to effectively eliminate the laser noise, which is common to all elements of the array, one must have laminar (non-turbulent) sample flow through the laser beam. This means that the aerosol inlet nozzle must be placed very close to the laser beam, typically 1.1–1.5 mm from beam center. Further, intracavity DPSSL particle counters are plagued by large amplitude bursts of noise, which occur infrequently at irregular intervals, and which disappear when the flow rate is reduced to sufficiently low levels. Since this excess noise is proportional to flow rate, it is referred to as flow noise. To prevent flow noise from producing false counts, detector thresholds must be set high enough to reject the worst case noise. This prevents achieving the best possible instrument sensitivity, which is defined by the molecular scattering noise limit. The Cerni et al. patent application publication cited above proposed that the flow noise is due to flow induced perturbations in the stray light field caused by air turbulence outside of the sample volume, which, in turn, is due to the proximity of the aerosol inlet nozzle to the sample volume. Thus, another apparently insurmountable problem ensues: If the aerosol inlet is located close to the sample volume, flow noise occurs, but if the aerosol inlet is far from the sample volume, laser noise occurs.

Accordingly, there is remains a need in the art for a particle counter system and method which provides high power illumination in a low noise environment without the need for expensive replacement of critical parts.

SUMMARY OF THE INVENTION

The invention solves the above problems by isolating the optical coatings from the sample flow. Preferably, the optical coating on the lasing material and the concave mirror of the laser cavity are isolated from the sample flow by Brewster windows.

In another aspect, the invention solves the above problems by providing a laser beam aperture assembly including an inner aperture closer to the inlet nozzle assembly and an outer aperture farther from the inlet nozzle assembly, with the distance of the outer aperture from the inner aperture being at least four times the distance from the inner aperture to the inlet nozzle assembly.

The invention provides a device for optically detecting an unconstrained particle suspended in a flowing fluid, the device comprising: a diode pumped solid state laser (DPSSL) including a lasing medium and a concave mirror defining a laser cavity, the lasing medium and concave mirror each having an optical coating on the end closest the other; an inlet nozzle assembly located between the lasing medium and the concave mirror; and a Brewster window located either between the optical coating on the lasing medium and the inlet nozzle assembly or between the optical coating on the concave mirror and the inlet nozzle assembly. Preferably, the Brewster window further comprises a first Brewster window located between the optical coating on the lasing medium and the inlet nozzle assembly and a second Brewster window located between the optical coating on the concave mirror and the inlet nozzle assembly. Preferably, the device includes a housing forming a sealed volume between the Brewster window and either the optical coating on the lasing medium or the optical coating on the concave mirror. Preferably, the fluid is a gas. Preferably, the device further includes a purge gas system directing a purge gas across the Brewster window. Preferably, the device further a cleaning port permitting the Brewster window to be cleaned without disassembling the DPSSL. Preferably, the device includes an aperture assembly including an inner aperture plate having an inner aperture and an outer aperture plate having an outer aperture farther from the inlet nozzle assembly than the inner aperture; and wherein the outer aperture is at least four times further from the inner aperture than the inner aperture is from the inlet nozzle assembly. Preferably, the outer aperture is at least five times further from the inner aperture than the inner aperture is from the inlet nozzle assembly. More preferably, the outer aperture is at least six times further from the inner aperture than the inner aperture is from the inlet nozzle assembly.

In another aspect, the invention provides a device for optically detecting an unconstrained particle suspended in a flowing fluid, the device comprising: a diode pumped solid state laser (DPSSL) having a laser cavity; an inlet nozzle assembly providing fluid sample flow within the laser cavity; and an aperture assembly comprising no more than two apertures, including an inner aperture plate having an inner aperture and an outer aperture plate having an outer aperture farther from the inlet nozzle assembly than the inner aperture; and wherein the outer aperture is at least four times further from the inner aperture than the inner aperture is from the inlet nozzle assembly. Preferably, the outer aperture is at least five times further from the inner aperture than the inner aperture is from the inlet nozzle assembly. More preferably, the outer aperture is at least six times further from the inner aperture than the inner aperture is from the inlet nozzle assembly. Preferably, the outer aperture is at least 35 mm from the inner aperture. Preferably, the inner surface of the inner aperture has an etched nickel finish. Preferably, the DPSSL includes a lasing medium and a concave mirror defining the laser cavity, and the device includes two of the aperture assemblies, one located between the lasing medium and the inlet nozzle assembly and the other located between the concave mirror and the inlet nozzle assembly.

In still another aspect the invention provides a device for optically detecting an unconstrained particle suspended in a flowing fluid, the device comprising: a diode pumped solid state laser (DPSSL) having a laser cavity producing a laser beam, the laser cavity including a lasing medium and a concave mirror; and an inlet nozzle assembly providing fluid sample flow within the laser cavity; wherein the inlet nozzle assembly comprises: an inner nozzle comprising, at its nozzle end, a thin-walled tube elongated along the direction of the laser beam and having a first nozzle end side facing the lasing medium and a second nozzle end side facing the concave mirror; and an outer light shield encircling the first nozzle end side and a single outer light shield encircling the second nozzle end side. Preferably, the outer light shield comprises a thin-walled tube. Preferably, there is only one of the light shields.

The invention provides a method for optically detecting an unconstrained particle suspended in a flowing fluid, the method comprising: providing a diode pumped solid state laser (DPSSL) including a lasing medium and a concave mirror defining a laser cavity, the lasing medium having an optical coating on an end facing the concave mirror and the concave mirror having an optical coating an end facing the lasing medium; directing a sample fluid flow into the laser cavity between the lasing medium and the concave mirror; and sealing the optical coatings from the sample flow. Preferably, the sealing comprises placing a first Brewster window between the optical coating on the lasing medium and the inlet nozzle assembly and placing a second Brewster window between the optical coating on the concave mirror and the inlet nozzle assembly. Preferably, the method further comprises directing a flow of essentially particle-free gas across the Brewster windows.

The invention not only provides a reliable, robust, DPSSL intracavity particle counter, but also provides such a particle counter that is capable of significantly more sensitivity than prior art particle counters. The above and other advantages of the present invention may be better understood from a reading of the following description of the preferred exemplary embodiments of the invention taken in conjunction with the drawings in which:

DETAILED DESCRIPTION OF THE PREFERRED EMBODIMENT

In this disclosure, the term light is not limited to visible radiation but is used in a broad sense meaning any electromagnetic radiation. It is also noted that this disclosure is limited to fluid particle counters, which is a term of art. There are particle counters that detect particle counters in a vacuum. Because there is no fluid present, or rather any fluid present is rarified as compared to normal fluids, problems associated with fluid flow, light scattering from the fluid and the apparatus used to control the fluid flow are absent and the physics of such particle counters is significantly different than that of fluid particle counters. Further, it should be noted that particle counters as disclosed herein are designed to be able to detect single particles which are unconstrained in a flowing fluid as distinguished from other systems that detect and analyze the particles of the fluid itself, clouds of particles suspended in a fluid, or particles which are constrained in the fluid, such as constrained to flow in a single line past a light beam. Those skilled in the art recognize that it is a much more difficult task to detect and size single particles flowing unconstrained in a fluid; therefore, the art of particle counting involves different technology than these other particle detection and analysis systems.

Figure 1:
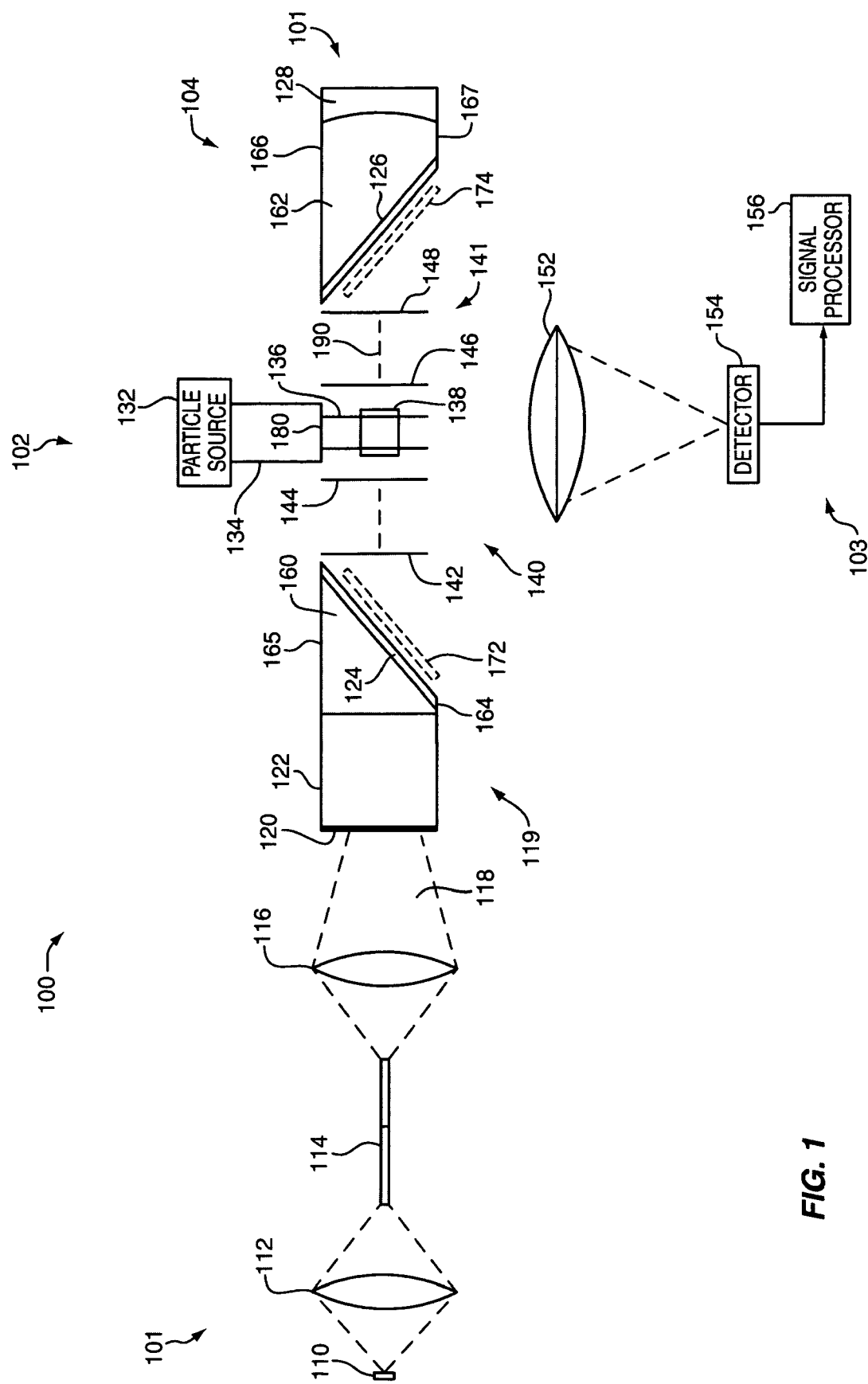
FIG. 1 is a schematic side view of a particle counter according to a preferred embodiment of the present invention.

FIG. 1 is a perspective view of a particle counter 100 according to the invention. Particle counter 100 includes optics assembly 101, flow chamber assembly 102, and detector assembly 103. Optics assembly 101 includes optical pump source 110, which pump source is preferably a laser diode, first lens assembly 112, fiber optic link 114, second lens assembly 116, and laser assembly 104. Laser assembly 104 includes a thin film coating forming mirror 120 (first mirror), solid state laser medium 122, Brewster windows 124 and 126, laser aperture assemblies 140 and 141, and laser beam reflector mirror 128 (second mirror). The laser cavity 119 is the portion between mirror 120 and mirror 128, and thus the lasing medium 122 and mirror 128 define the laser cavity of the intracavity laser 104. Preferably, aperture assembly 140 includes aperture plates 142 and 144 and aperture assembly 141 includes aperture plates 146 and 148. In addition, the particle counter 100 includes a Brewster window purge gas system 172 and 174. Purge gas system 172, 174 preferably utilizes filtered purge air.

Flow chamber assembly 102 preferably includes particle source 132 and inlet nozzle assembly 134, which together create flow jet 136. Detector assembly 103 preferably includes collection optics 152, detector 154, and signal processor 156. The beam 190 of laser 104, the flow jet 136, and most importantly, detector 103 determines detecting region 138. As discussed in the prior art, the detector is important in determining the detecting region 138, which is the volume from which light can get into the detector 154. This is shown to have boundaries in the horizontal direction slightly larger than the boundaries of the flow jet 136, though it could just as well have boundaries the same size as or smaller than the boundaries of flow jet 136. As will be seen in more detail below, an important aspect of the invention is that very little stray light scattered from inlet nozzle 134, aperture assemblies 140 and 141 and other optical components gets into detecting region 138. Here, the term "scattered" is used in the broad sense that includes reflected, defracted, refracted, and scattered light. That is, stray light includes any light that, if it got into detecting region 138, could interfere with or degrade the signal from the light scattered by particles in the jet 138 which are intended to be counted. As known in the art, the collecting optics 152 of a particle counter is not designed to form an image of the particle on the detector 154, but rather is designed to maximize the amount of light from the detecting region 138 that falls on the detector 154. In such optics systems, light from areas outside the detecting region 138 can be incident on the detector 154, although the farther from the detecting region 138 that the light source is located, the lesser will be the intensity of the light when it gets to the detector 154.

The laser volume 160 between Brewster window 124 and lasing medium 122 and the laser volume 162 between Brewster window 126 and mirror 128 are sealed, as indicated by the lines 164, 165, 166, and 167 schematically showing a sealed housing. Brewster windows 124 and 126 provide protection for the thin film optical coatings on the right side of lasing medium 122 and the left side of mirror 128, while introducing minimal additional laser cavity losses, and therefore minimal reduction in intracavity power. That is, the solid state lasing crystal 122 and concave mirror 128 are mounted behind windows, in sealed compartments, to shield them from sample flow 126. Windows 124 and 126 are made from an uncoated, robust, optical material, which has a much higher damage threshold than the thin film optical coatings. Reflection losses for uncoated optical windows are far greater than for coated windows. The invention overcomes this problem by mounting both windows at the Brewster's angle. Theoretically, reflection losses can approach zero, for plane polarized light incident on a window which is positioned at the Brewster's angle. Solid state laser radiation is not naturally plane polarized, however for certain birefringent crystals such as Nd:YLF and Nd:YVO$_4$, placement of one Brewster's window within the cavity, can force it to be plane polarized, and in a preferred direction. Window surface roughness and microscratches can result in cavity losses due to surface scattering. Thus, preferably, windows 124 and 126 are polished to a super polish specification, far better than that available on typical commercial optics. Furthermore, preferably the window bulk scatter is reduced to a minimum by fabricating the windows from fused silica, preferably Suprasil® 311, or other defect-free optical glass. For fused silica, Brewster's angle is 55.4° at 1053 nm. When inserted intracavity, the two Suprasil 311 Brewster's windows result in a loss in cavity power of less than or equal to 10%, which is not significant when compared to the loss in power caused by pitted or contaminated coatings.

Laboratory experiments were conducted to demonstrate that the Suprasil 311 Brewster's windows were much more robust and damage resistant than the thin film optical coatings. An open air optical bench was configured, similar to the instrument described in the Mitchell reference above, to allow easy access to the windows. Several types of particulate contamination were deposited on the Suprasil 311 windows, including very large particles produced by sanding a block of aluminum. The latter has never been attempted with thin film optical coatings, as such action would certainly destroy the coatings. Particle deposition occurred with and without lasing in the cavity. None of these tests resulted in burning and pitting of the surface layer, as has often been observed with thin film optical coating damage. Only one experiment resulted in damage to a Suprasil 311 window, and that damage appeared as a tiny crack in the bulk glass, likely the result of a large aluminum particle melting in the laser beam 190, then impacting the Suprasil 311 window and fracturing the glass via a thermal shock mechanism. In actual commercial use, such large particles should not be present.

The purge gas feature known in the prior art has been retained in the particle counter according to the invention, except now the purge gas, which is an essentially particle-free gas, is directed across the two Brewster's windows 124 and 126, as indicated by the purge gas ventilation slots 172 and 174. Preferably, the purge gas is filtered air. Furthermore, cleaning ports have been added such the windows can be cleaned without disassembling the instrument.

Figure 2:
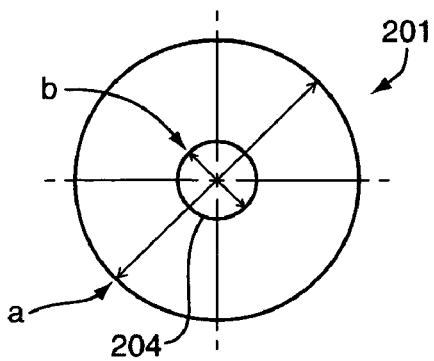
FIG. 2 is a plane view of an aperture plate of the particle counter of FIG. 1.
Figure 3:
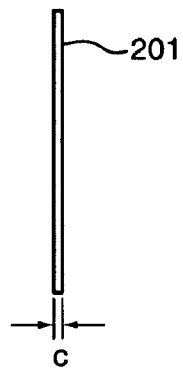
FIG. 3 is a side view of an edge of the aperture plate shown in FIG. 2.

FIGS. 2 and 3 show a typical one 201 of apertures 142, 144, 146 and 148. The apertures plates are preferably circular, each having a preferably circular aperture 204. The dimensions a, b, and c of each aperture plate is discussed below.

Figure 4:
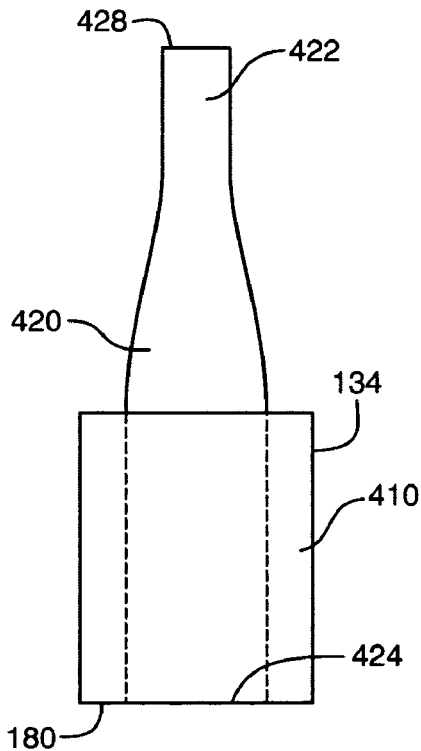
FIG. 4 is a side plane view of the preferred aerosol inlet nozzle of the particle counter of FIG. 1.
Figure 5:
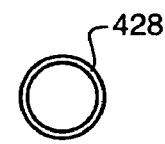
FIG. 5 is a top end view of the aerosol nozzle of FIG. 4.
Figure 6:
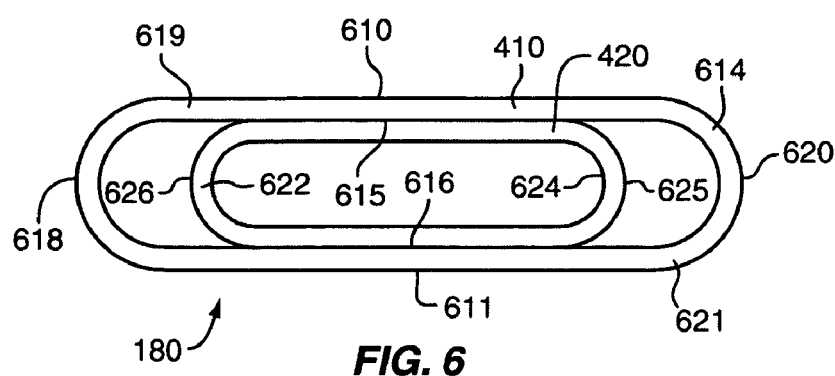
FIG. 6 is a bottom end view of the aerosol nozzle of FIG. 4.

FIGS. 4, 5 and 6 show inlet nozzle assembly 134. Inlet nozzle includes an inner inlet tube 420 and an outer light shield 410. One end 428 of inner inlet tube 420 is preferably circular or other suitable shape to connect to particle source 122. Nozzle end 424 is flattened into the elongated form best shown in FIG. 6. Outer light shield 410 is preferably formed by a larger size tube which is also flattened to follow the contour of flattened nozzle end 424. The outer tube 410 preferably encircles the nozzle end 424. A feature of the invention is that there is only single light shield on each side of the nozzle end 424, as compared to the pair of light shields in the prior art. However, there can also be multiple light shields. Another feature is that end 618 of tube 410 forms a first light shield 619 encircling the first side 626 of nozzle end 524 and end 620 of tube 410 forms a single second light shield 621 encircling second side 625 of nozzle end 424. Here, encircles means that if a line is drawn perpendicular to the direction of the laser beam and tangent to the side end, such as 626, of the nozzle, the light shield and the perpendicular line will form a closed loop. Another feature of the invention is that the light shield 618 and the light shield 620 each has the same length as the nozzle end 424; that is the light shields 618 and 620 do not extend further into the laser cavity than the nozzle end 424. Orienting the nozzle assembly of FIGS. 4 and 6 with respect to FIG. 1, the elongated direction of nozzle end 180, i.e., the horizontal dimension in FIGS. 4 and 6 is along the direction of laser beam 190, with sides 618 and 626 face lasing medium 122 and sides 625 and 620 face concave mirror 620.

Apertures 142, 144, 146 and 148 and light shield 410 provide improved stray light containment over prior art particle counters. A feature of the invention is that each of the two the light traps 140 and 141 along the laser beam have been simplified, such that each preferably contains only two apertures, in place of the five disclosed in the prior art. The apertures plate 142 closest to the laser crystal 122 and the aperture plate 148 closest to the concave mirror 128 preferably have apertures 204 having a diameter b (FIG. 2) of 2.0 mm, while the apertures 204 in aperture plates 144 and 146 closest to the sample volume 138 are preferably 1.4 mm in diameter. Preferably, the inner aperture plates 144 and 146 are positioned 5 mm from the edges of the sample volume. Preferably, the outer aperture plates 142 and 144 are spaced at least 35 mm apart as are the outer aperture plates 146 and 148. The 1.4 mm apertures nearest the sample nozzle are the primary light shields, with the 2.0 mm outboard apertures serving a secondary role. In the preferred embodiment, outer diameter "a" (FIG. 2) of aperture plates 201 equals 0.248 inches with a tolerance of +0.000/−0.002 inches, although aperture plates having other diameters may be used. Aperture plates 201 are preferably made of black anodized aluminum, though other suitable metals, plastics, or other materials may be used. Preferably, the inner face of each inner aperture plate 144 and 146 has an etched nickel finish such as may be provided by Custom Microwave, Inc., which shows lower reflectance than any known absorbing paint, although other low reflectance finishes may also be used. It is important that the aperture plates be made very thin, so that the apertures 204 can be accurately controlled. Preferably, the apertures 204 are made by a photo engraving process, or other process that can be accurately controlled. Aperture plates 201 preferably have a thickness "c" (FIG. 3) of 0.005 inches, although other thicknesses may be used.

The inlet tube portion 420 of inlet nozzle assembly 134 is preferably made from annealed brass, thin walled, round tube, which has been crushed about a form, to provide an air flow path at nozzle 424 of approximately 0.6×10.0 mm. The nozzle portion 424 of inner tube 420 is the preferably mounted inside another thin walled, shaped brass tube 410, with inside dimensions of approximately 1.5×16.0 mm. In the preferred embodiment, the distance from the end of side 618 to the end of side 620 of outer tube 410 is approximately 0.655 inches, the distance from the end of side 626 to the end of side 625 of inner inlet nozzle 424 is 0.419 inches, the distance between points 610 and 611 on the outer side walls of outer light shield tube 410 is 0.090 inches, the distance between points 615 and 616 on the outer side wall of inner tube 420 is 0.059 inches. Both tube 420, and tube 419 are preferably thin-walled tubes, which is a term known in the art meaning-that the thickness of the tube is much thinner than the largest diameter of the tube, preferably at leas five times thinner. Preferably, the wall thickness of both tubes is 0.014 inches. Preferably, the circular radius of the outer tube ends, such as 614 is approximately 0.045 inches.

The outer light shield tube 410 does not carry any air flow, however it does an excellent job of shadowing the inner, aerosol nozzle 420. The ends 618 and 620 of the light shield tube 410 are illuminated by stray light emitted from the laser beam light traps, however these illuminated ends are now farther from the sample volume 138, and thus can be more effectively rejected by the optical system which images the sample volume onto the multi-element detector array. The outer surface of the aerosol nozzle 424, plus both surfaces of the outer tube 410, are painted with a high performance, optical black paint, such as Cardinal Velvethane™ or 3M Nextel™.

An important feature of the invention is that the apertures in the outer aperture plates 142 and 148 are sufficiently far from the apertures in the inner aperture plates 144 and 146, respectively, that light that passes through the outer apertures cannot strike the end 180 of the inlet nozzle assembly 136. If the inner aperture plates 144 and 146 are placed closer to detection region 138, and thus the inlet nozzle assembly, the apertures in the outer aperture plates 142 and 148 can be placed close to the apertures in the inner aperture plates 144 and 146, respectively. Thus, a teaching of the invention is that the distance between the inner and outer aperture plates should be significantly larger than the distance between the inner aperture plates 144 and 145 and the end 180 of the inlet nozzle assembly. Preferably, the outer apertures are at least at least four times further from the inner aperture than the inner aperture is from the inlet nozzle assembly. More preferably, the outer apertures are at least at least five times further from the inner aperture than the inner aperture is from the inlet nozzle assembly. Most preferably, the outer apertures are at least at least six times further from the inner aperture than the inner aperture is from the inlet nozzle assembly.

This invention provides a reliable, robust, DPSSL intracavity particle counter. As such, it removes a major barrier to commercial product success. The particle counter according to the invention is designed to have a first channel sensitivity of 0.055 to 0.060 microns and a 1 cubic foot per minute (cfm) sample flow rate.

There has been described a novel DPSSL intracavity particle counter system. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. For example, if only one of the optical coatings on the lasing cavity and the concave mirror were isolated by a Brewster window, the system would still be more robust than prior art systems. As another example, although the invention has been described in connection with an aerosol particle counter in which the fluid is a gas, it could also be applied to a liquid particle counter. As another example, the light collector, such as 152, may be replaced with a wide variety of other collectors ranging from a simple collector, such as a single photodetector, to very complex systems using a large number of lenses and/or mirrors and/or multiple detectors. Similarly, nozzle assemblies and aperture assemblies as shown in the prior art may be used. It is also evident that the methods recited may in many instances be performed in a different order; or equivalent structures and processes may be substituted for the various structures and processes described. Consequently, the invention is to be construed as embracing each and every novel feature and novel combination of features present in and/or possessed by the DPSSL intracavity particle counter herein described.

We claim:

1. A device for optically detecting an unconstrained particle suspended in a flowing fluid, said device comprising:
   a diode pumped solid state laser (DPSSL) including a basing medium and a concave mirror defining a laser cavity, said lasing medium and concave mirror each having an optical coating on the end closest the other;
   an inlet nozzle assembly located between said lasing medium and said concave mirror; and
   a Brewster window located either between said optical coating on said lasing medium and said inlet nozzle assembly or between said optical coating on said concave mirror and said inlet nozzle assembly.

2. A device as in claim 1 comprising a first said Brewster window located between said optical coating on said lasing medium and said inlet nozzle assembly and a second said Brewster window located between said optical coating on said concave mirror and said inlet nozzle assembly.

3. A device as in claim 1 and further including a housing forming a sealed volume between said Brewster window and either said optical on said lasing medium or said optical on said concave mirror.

4. A device as in claim 1 wherein said fluid is a gas.

5. A device as in claim 1 and further including a purge gas system directing a purge gas across said Brewster window.

6. A device as in claim 1 and further including a cleaning port permitting said Brewster window to be cleaned without disassembling said DPSSL.

7. A device as in claim 1 and further including an aperture assembly including an inner aperture plate having an inner aperture plate having an outer aperture farther from said inlet nozzle assembly than said inner aperture; and wherein said outer aperture is at least four times further from said inner aperture than said inner aperture is from said inlet nozzle assembly.

8. A device as in claim 7 wherein said outer aperture is at least five times further from said inner aperture than said inner aperture is from said inlet nozzle assembly.

9. A device as in claim 7 wherein said outer aperture is at least six times further from said inner aperture than said inner aperture is from said inlet nozzle assembly.

10. A device for optically detecting an unconstrained particle suspended in a flowing fluid, said device comprising:
    a diode pumped solid state laser (DPSSL) having a laser cavity;
    an inlet nozzle assembly providing fluid sample flow within said laser cavity; and
    an aperture assembly comprising no more than two apertures, including an inner aperture plate having an inner aperture and an outer aperture plate having an outer aperture farther from said inlet nozzle assembly than said inner aperture; and
    wherein said outer aperture is at least four times further from said inner aperture than said inner aperture is from said inlet nozzle assembly.

11. A device as in claim 10 wherein said outer aperture is at least five times further from said inner aperture than said inner aperture is from said inlet nozzle assembly.

12. A device as in claim 10 wherein said outer aperture is at least six times further from said inner aperture than said inner aperture is from said inlet nozzle assembly.

13. A device as in claim 10 wherein said outer aperture is at least 35 mm from said inner aperture.

14. A device as in claim 10 wherein the inner surface of said inner aperture has an etched nickel finish.

15. A device as in claim 10 wherein said DPSSL includes a lasing medium and a concave mirror defining said laser cavity, said device including two of said aperture assemblies, one located between said lasing medium and said inlet nozzle assembly and the other located between said concave mirror and said inlet nozzle assembly.

16. A method for optically detecting an unconstrained particle suspended in a flowing fluid, said method comprising:
    providing a diode pumped solid state laser (DPSSL) including a lasing medium and a concave mirror defining a laser cavity, said lasing medium having an optical on an end facing said concave mirror and said concave mirror having an optical coating an end facing said lasing medium;
    directing a sample fluid flow into said laser cavity between said lasing medium and said concave mirror; and
    sealing said optical coatings from said sample flow.

17. A method as in claim 16 wherein said sealing comprises placing a first Brewster window between said optical on said lasing medium and said inlet nozzle assembly and placing a second Brewster window between said optical coating on said concave mirror and said inlet nozzle assembly.

18. A method as in claim 17 and further comprising directing a flow of essentially particle-free gas across said Brewster windows.

* * * * *